US00PP30593P3

(12) United States Plant Patent
Wood

(10) Patent No.: US PP30,593 P3
(45) Date of Patent: Jun. 25, 2019

(54) ***BERBERIS* PLANT NAMED 'SMBTJ'**

(50) Latin Name: *Berberis thunbergii*
Varietal Denomination: SMBTJ

(71) Applicant: Timothy Wood, Spring Lake, MI (US)

(72) Inventor: Timothy Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 15/732,263

(22) Filed: Oct. 16, 2017

(65) Prior Publication Data

US 2019/0116703 P1 Apr. 18, 2019

(51) Int. Cl.
*A01H 5/12* (2018.01)

(52) U.S. Cl.
USPC ..... Plt./241

(58) Field of Classification Search
USPC ..... Plt./241
CPC ... A01H 5/12; A01H 5/00; A01H 5/02; A01H 5/08; A01H 6/00
See application file for complete search history.

*Primary Examiner* — June Hwu
(74) *Attorney, Agent, or Firm* — Cassandra Bright

(57) ABSTRACT

A new and distinct *Berberis* cultivar named 'SMBTJ' is disclosed, characterized by yellow young foliage with an orange flush. Plants have foliar resistance to sun burn and are compact and rounded in habit. The new variety is a *Berberis*, normally produced as an outdoor garden or container plant.

2 Drawing Sheets

Latin name of the genus and species: *Berberis thunbergii*.
Variety denomination: 'SMBTJ'.

BACKGROUND OF THE INVENTION

The new *Berberis* cultivar is a product of a planned breeding program conducted by the inventor, Timothy D. Wood, in Grand Haven, Mich. The objective of the breeding program was to produce new *Berberis* varieties. The cross resulting in this new variety was made during June of 2003.

The seed parent is an unpatented, commercial variety *Berberis thunbergii* 'Golden Pygmy'. The pollen parent is unknown, as it was an open pollination breeding program. The new variety was identified as a potentially interesting selection in June of 2006, at a commercial greenhouse in Grand Haven, Mich.

Asexual reproduction of the new cultivar 'SMBTJ' by softwood to semi-hardwood cuttings was first performed during the June of 2006, at a commercial greenhouse in Grand Haven, Mich. Subsequent propagation has shown that the unique features of this cultivar are stable and reproduced true to type in 4 successive generations.

SUMMARY OF THE INVENTION

The cultivar 'SMBTJ' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMBTJ' These characteristics in combination distinguish 'SMBTJ' as a new and distinct *Berberis* cultivar:

1. Vibrant foliage colored yellow and yellow-green flushed orange when young and yellow-green, stippled yellow with maturity.

2. Compact, rounded habit.
3. Orange flush on new growth.
4. Foliar resistance to burning in full sun.

PARENT COMPARISON

Plants of the new cultivar 'SMBTJ' are similar to plants of the seed parent, unpatented, commercial variety *Berberis thunbergii*, 'Golden Pygmy' in most horticultural characteristics, however, plants of the new cultivar 'SMBTJ' differ in the following;

1. The new variety has foliage with stronger resistance to burning in full sun, the seed parent is susceptible to foliar burning in full sun.
2. Compact, rounded habit. The seed parent is larger with a less compact habit.

Pollen parent unknown as this is product of open pollination.

COMMERCIAL COMPARISON

Plants of the new cultivar 'SMBTJ' can be compared to the commercial variety *Berberis* 'Koren', U.S. Plant Pat. No. 24,818. These varieties are similar in most horticultural characteristics; however 'SMBTJ' differs in the following:

1. Plant habit of the new variety is smaller and more compact than this comparator.
2. Foliage of the new variety is more yellow in full sun than this comparator.

BRIEF DESCRIPTION OF THE PHOTOGRAPHS

Figure 1:
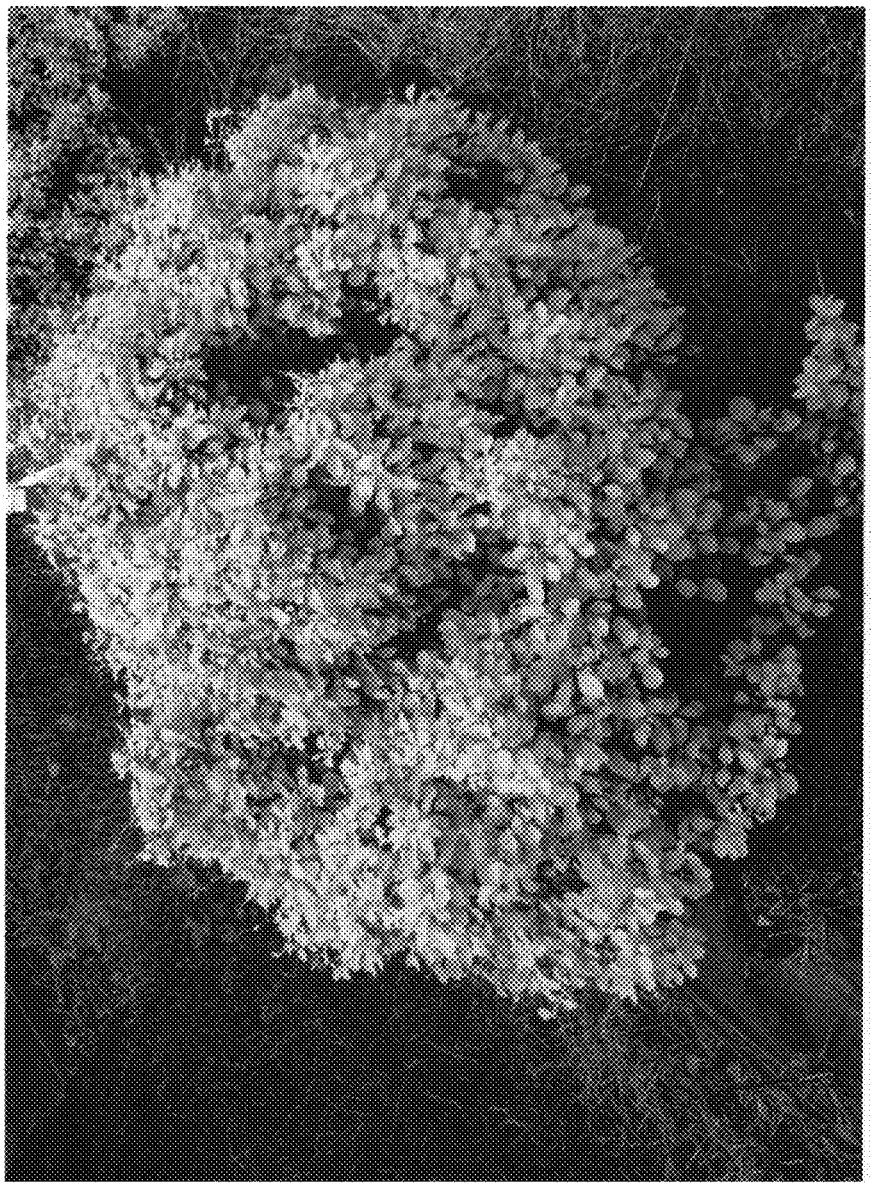

The accompanying photograph in FIG. 1 illustrates in full color a typical plant of 'SMBTJ' during Spring, with vibrant yellow Summer foliage, grown in a 2 gallon pot, in Grand Haven, Mich.

Figure 2:
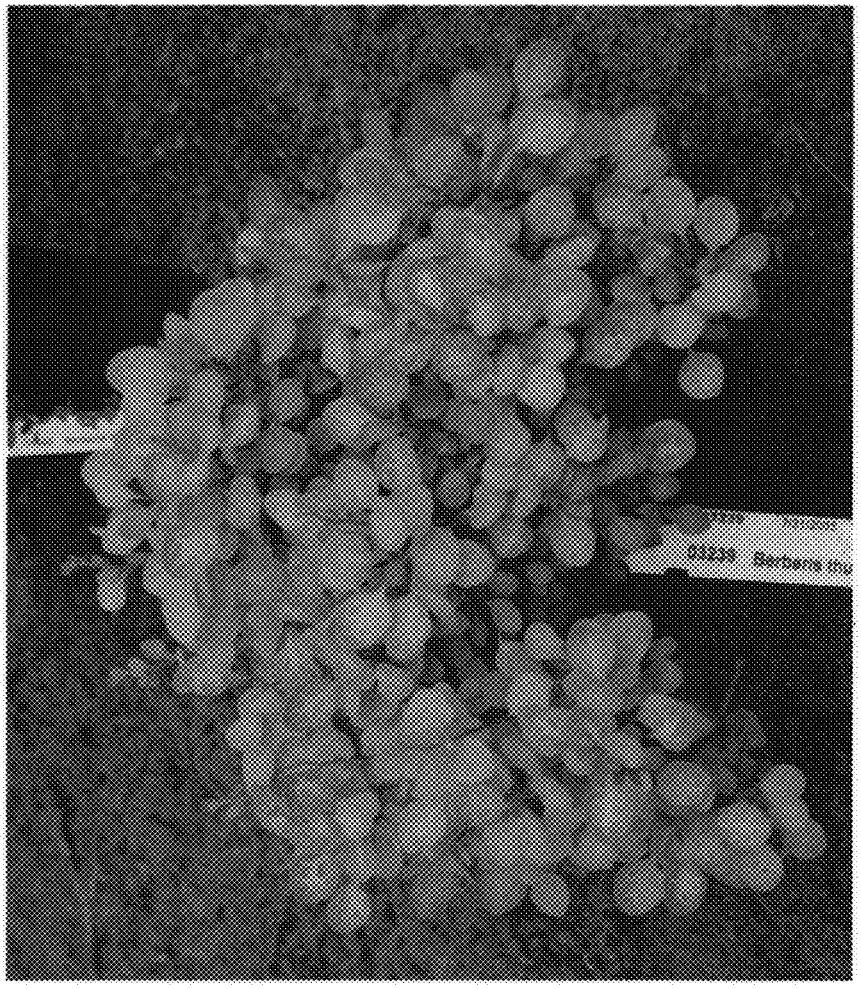

FIG. 2 illustrates in full color a typical plant of 'SMBTJ' during Spring, with new growth. Age of the plant photographed is approximately 2 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'SMBTJ' plants grown out doors and also in a commercial poly greenhouse in Grand Haven, Mich. under natural lighting. Measurements were taken during the Spring and Summer of 2015. The plants were 2-3 years old in 1 gallon containers and field grown. The growing temperature ranged from 5° C. to 27° C. Measurements and numerical values represent averages of typical plant types.

Botanical classification: *Berberis thunbergii* 'SMBTJ'.

PROPAGATION

Time to initiate roots: About 20 days at approximately 27° C.

Root description: Density is moderate to dense, fibrous, freely branching. Medium root thickness. White to brown in color, not effectively measured with a color chart.

Time to produce a rooted young plant: About 90 days at 27° C.

PLANT

Plant type: Perennial, deciduous shrub.

Age of plant described: Approximately 2-3 years old.

Growth habit: Good.

Pot size of plant described: 1 gallon nursery pot, also field grown plants.

Overall plant shape: Upright/rounded.

Height: 50 cm in 4 year old field plant.

Plant spread: 90 cm in 4 year old field plant.

Growth rate: Good.

Plant vigor: Good.

Branching characteristics: Upright, strong basal branching. Pinching required.

Length of primary lateral branches: 35-50 cm in 4 year old field plant.

Diameter of lateral branches: 2.5 mm.

Quantity of lateral branches: 35 on a 4 year old field plant.

Stem:

- *Stem appearance*.—Round.
- *Stem strength*.—Strong.
- *Stem color*.—New growth near Yellow-Group 3C. Older stem near Yellow-Green 144A.
- *Bark*.—Near RHS Grey 201A.
- *Pubescence*.—None.
- *Aspect*.—Straight, occurring at 0-45° angles from the center of plant.

Internode length: 0.5-1 cm.

FOLIAGE

Leaf:

- *Arrangement*.—Sub-opposite to alternate.
- *Leaf shape*.—Ovate.
- *Average length*.—2.0 cm.
- *Average width*.—1-1.25 cm.
- *Apex*.—Acute to obtuse.
- *Base*.—Attenuate.
- *Margin*.—Entire.
- *Texture of top surface*.—Smooth, soft.
- *Texture of bottom surface*.—Slightly rough, somewhat grainy feel.
- *Color*.—Young foliage upper side: Near RHS Yellow 3C with slight stippling of Yellow-Green 144A; flushed Orange 28A. Young foliage under side: Green-Yellow 1C with slight stippling of Yellow-Green 144D, flushed Orange 26A. Mature foliage upper side: Near RHS Yellow-Green 144A. Mature foliage under side: Near RHS Yellow-Green 146C with slight stippling of Yellow 3C. Fall foliage: Color change not observed. Venation: Pattern: Pinnate. Color upper side: Near RHS Yellow-Green 146C. Color under side: Near RHS Yellow-Green 146C.
- *Petiole*.—Average Length: 5 mm. Diameter: 1 mm. Petiole color upper side: Near RHS Yellow-Green 144A with slight stippling of Yellow-Group 3C. Petiole color lower side: Near RHS Yellow-Green 146D with slight stippling of Yellow 3C. Petiole Texture upper side: Smooth. Petiole Texture lower side: Smooth.
- *Thorns*.—Form: Attached to plant nodes 1 cm in length. Simple. Color new: Near RHS Greyed-Orange 165A with stippling of Greyed-Yellow Group 160B. Attached to new growth nodes, 2 mm long.
- *Stipules*.—Brown-Group 200C base of leaf petiole, linear, 1 mm long.

FLOWER

Natural flowering season: Spring.

Inflorescence type and habit: Terminal umbellate fascicles.

Flower longevity on plant: 2 weeks.

Quantity of flowers per inflorescence: 1-3.

Quantity of flowers per plant: Average 102.

Individual flowers:

- *Flower shape*.—Star shaped.
- *Flower aspect*.—Outwardly to drooping.
- *Flowering arrangement*.—Terminal.
- *Size*.—Diameter: Approximately 5 mm. Depth: Approximately 9 mm.
- *Flower other characteristics*.—Persistence: Self cleaning. Fragrance: Not noted.

Bud:

- *Shape*.—Rounded, globose.
- *Length*.—3-4 mm.
- *Diameter*.—3-4 mm.
- *Color*.—Near RHS Greyed-purple 187A.

Petal:

- *Petal arrangement*.—Whorl.
- *Number of petals per flower*.—5-6.
- *Petal shape*.—Elliptic.
- *Petal base*.—Obtuse.
- *Margin*.—Entire.
- *Tip shape*.—Obtuse.
- *Length*.—4 mm.
- *Width*.—3 mm.
- *Texture*.—Upper: Smooth. Lower: Smooth.

Petal color:

*When opening*.—Upper surface: Near RHS Yellow 12C flushed close to Red 46A to 46B throughout. Lower surface: Near RHS Yellow 12C.

*Fully opened*.—Upper surface: Near RHS Yellow 12C. Lower surface: Near RHS Yellow 12D.

Sepal:

*Arrangement*.—Whorl.

*Appearance*.—Smooth.

*Number*.—6.

*Shape*.—Roughly orbicular.

*Tip*.—Acute to obtuse.

*Base*.—Acute to obtuse.

*Margin*.—Entire.

*Length*.—4 mm.

*Width*.—3 mm.

*Texture, upper*.—Smooth.

*Texture, lower*.—Smooth.

*Color*.—Upper surface at maturity: Near RHS Yellow-green 145B. Under surface at maturity: Near RHS Yellow-green 145B.

Peduncle:

*Length*.—6 mm.

*Diameter*.—1-3 mm.

*Color*.—Near RHS Yellow-Green 146B.

*Orientation*.—Upright/outward.

*Strength*.—Good.

*Texture*.—Smooth/glabrous.

REPRODUCTIVE ORGANS

Stamens:

*Number*.—6.

*Filament length*.—About 1 mm.

*Filament color*.—Near RHS green 137B.

Anthers:

*Shape*.—Globular.

*Length*.—About 1 mm.

*Color*.—Near RHS Yellow 12A.

*Pollen color*.—Near RHS Yellow 12A.

*Pollen amount*.—Some.

Pistil:

*Number*.—1 per flower.

*Length*.—About 3 mm.

*Style*.—Length: About 3 mm. Color: Near RHS Green-white 157B.

*Stigma*.—Color: Near RHS Green-white 157B.

OTHER CHARACTERISTICS

Seeds and fruits: 1-3 fruit per branch. 20 fruit per plant. Fruits approximately 1 cm long and 6 mm in diameter. Colored near Orange N25D, with an Orange-Red 34A overlay. Texture is glabrous. Seed production not observed to date.

Disease/pest resistance: Neither resistance nor susceptibility to normal diseases and pests of *Berberis* have been observed.

Temperature tolerance: The new variety tolerates temperatures between −31° C. to 38° C.

What is claimed is:

1. A new and distinct cultivar of *Berberis* plant named 'SMBTJ' as herein illustrated and described.

* * * * *